(12) United States Patent
Lackey

(10) Patent No.: US 7,745,692 B2
(45) Date of Patent: Jun. 29, 2010

(54) ENLARGEMENT AND NEW USE OF SOYBEAN ENDOSPERM TISSUE

(76) Inventor: James A. Lackey, 615 North Carolina Ave. SE., Washington, DC (US) 20003

( * ) Notice: Subject to any disclaimer, the term of this patent is extended or adjusted under 35 U.S.C. 154(b) by 497 days.

(21) Appl. No.: 11/527,096

(22) Filed: Sep. 26, 2006

(65) Prior Publication Data
US 2007/0101456 A1 May 3, 2007

Related U.S. Application Data

(60) Provisional application No. 60/733,157, filed on Nov. 2, 2005.

(51) Int. Cl.
*A01H 1/04* (2006.01)
*A01H 3/00* (2006.01)
*A01H 1/00* (2006.01)
(52) U.S. Cl. .................. 800/266; 800/269; 800/263
(58) Field of Classification Search ................. None
See application file for complete search history.

(56) References Cited

U.S. PATENT DOCUMENTS

| 3,116,281 | A | 12/1963 | Tookey et al. | |
|---|---|---|---|---|
| 2004/0093642 | A1* | 5/2004 | Scott | 800/287 |
| 2004/0143871 | A1* | 7/2004 | Dhugga | 800/284 |
| 2005/0160494 | A1* | 7/2005 | Singletary et al. | 800/281 |

OTHER PUBLICATIONS

Chen et al 2004 Crop Science 44:316-325, reference provided by applicant.*
U.S. Appl. No. 10/713,836, filed Jul. 22, 2004, Dhugga, K. S.
Dhugga, K. et al. 2004. Guar seed beta-manna synthase is a member of the cellulose . . . Science 303: 363366.
Aspinall, G. O., and J. N. C. Whyte. 1964. Polysaccharides of soybeans. part i. galactomanans from the hulls. J. Chem. Soc. 232:5058-5063.
Baker, Daniel M., and Harry C. Minor. 1987. Frequency and comparative anatomy . . . genotypes. Crop Sci. 27:1301-1303.
Buckeridge, M. S., S. M. C. Dietrich, and D. U. de Lima. 2000. Galactomannans . . . legume seeds. pp. 283-316 in Gupta, A. K., and N. Kaur. Carbohydrate Reserves. Elsevier.
Chen, Yiwu, and Randall L. Nelson. 2004. Genetic variation and relationships among cultivated, wild, and semiwild soybean. Crop Sci. 44(1):316-325.
Dhugga, Kanwarpal S., et al. 2004. Guar seed B-mannan synthase is a member of the cellulose synthase super gene family. Science 303:363-366.
Holmgren, Patricia K., Noel H. Holmgren, and Lisa C. Barnett. 1990. Index herbarorium. Part I: The herbaria of the world. 8th. ed. Regnum Veg. vol. 120. x+693 pp. New York.
Hymowitz, T., and R. J. Singh. 1987. Taxonomy and speciation. pp. 23-48 in Wilcox, J. R. 1987. Soybeans: improvement, production, and uses. Second edition. xxi+888 pp. ASA.
Kirkbride, Joseph H. Jr., Charles R. Gunn, and Anna L. Weitzman. 2003. Fruits and seeds of genera in the subfamily Faboideae (Fabaceae). USDA ARS Technical Bulletin 1890:v+.
Kopooshian, Haig. 1963. Seed character relationships in the Leguminosae. Ph.D. dissertation. iv+160 pp. Iowa State University, Ames.
Kopooshian, Haig, and Duane Isely. 1966. Seed character relationships in the Leguminosae. Iowa Academy of Science 73:59-67.
Lackey, J. A. 1981. Phaseoleae. pp. 301-327 in Polhill, R. M., and P. H. Raven. 1981. Advances in legume systematics. part 1. xvi+425+xxi pp. Royal Botanic Gardens, Kew.
Lackey, James A. 1981. Systematic significance of the epihilum in Phaseoleae (Fabaceae, Faboideae). Botanical Gazette 142(1):160-164.
Ma, Fengshan, Carol A. Peterson, and Mark Gijzen. 2004. Reassessment of the pits and antipits in soybean seeds. Canadian Journal of Botany 82:654-662.
Nadelmann, Hugo. 1890. Ueber die Schleimendosperme der Leguminosen. Prings. Jarhb. Wissen. Bot. 21:609-691+6 ic., p. 687 p. 629.
Pammel, L. H. 1899. Anatomical characters of the seeds of Leguminosae, chiefly genera of Gray's manual. Trans. Acad. Sci. St. Louis 9(6):91-273+xxxv ic..
Sterling, Clarence. 1954. Development of the seed coat of lima bean (*Phaseolus lunatus* L.). Bull. Torrey Bot. Club 81(4):271-287.
Thorne, John H. 1981. Morphology and ultrastructure of maternal seed tissues of soybeans in relation to the import of photosynthate. Plant Physiology 67:1016-1025.
Tookey, H. L., and Quentin Jones. 1965. New sources of water-soluble seed gums. Economic Botany 19:165-171.
Whistler, Roy L., and Jouko Saarnio. 1957. Galactomannan from soy bean hulls. J. Am. Chem. Soc. 79(22):6055-6057.

(Continued)

*Primary Examiner*—Anne Marie Grunberg
*Assistant Examiner*—Brent Page
(74) *Attorney, Agent, or Firm*—Dodds and Associates; Leca S. Somersalo; John Dodds

(57) ABSTRACT

The invention relates to genetic manipulation and evaluation of soybean seed, particularly for the enlargement and use of endosperm tissue for galactomannan gum extraction. A method for combining several elements which have heretofore been misunderstood or were unknown, is presented. The resulting enlarged endosperm tissue has many commercial uses.

16 Claims, 1 Drawing Sheet

OTHER PUBLICATIONS

Wolf, Walter J., David J. Sessa, Y. Victor Wu, and Arthur R. Thompson. 2002. Air classification of pin-milled soybean hulls. Cereal Chem. 79(3):439-444.

Yaklich, R. W., E. L. Vigil, and W. P. Wergin. 1989. The pit and antipit in the genus Glycine. Crop Sci. 29:1304-1309.

* cited by examiner

ENLARGEMENT AND NEW USE OF SOYBEAN ENDOSPERM TISSUE

FIELD OF THE INVENTION

The invention generally relates to genetic manipulation and evaluation of soybean seed, particularly for the enlargement and use of endosperm tissue for gum extraction.

BACKGROUND OF THE INVENTION

Dormant seeds of many legumes have been long known to store polysaccharide gums in the middle endosperm layer (Schleiden and Vogel. 1839. Nova Acta Acad. Caesar. Leop.-Carol. 19(1):53-96+6 ic; Nadelmann. 1890. Prings. Jarhb. Wissen. Bot.21:609-691+6 ic.;

Kopooshian and Isely, 1966. Iowa Acad. Sci. 73:59-67). These polysaccharide gums, which are primarily galactomannans, are able to produce gels or viscous solutions at low concentrations, which makes them valuable for many purposes. Also, because the gums are localized in the endosperm, extraction can be accomplished easily by several simple chemical and mechanical means. Although used since antiquity, they have become increasingly valuable for food, cosmetics, pharmaceuticals, textiles, paper, and a wide variety of industrial uses starting in the 1940's (Buckeridge et al. 2000. 283-316 in Gupta and Kuar, eds.

Carbohydrate Reserves in Plants—Synthesis and Regulation. Elsevier). The primary current sources of galactomannans are guar (*Cyamopsis tetragonoloba*), locust (*Ceratonia siliqua*), and fenugreek (*Trigonellafoenum-graecum*), all of which are imported and subject to supply and price uncertainties (Dhugga et al. 2004. Science 303:363-366).

Scientists have for decades attempted to find a good domestic plant source of galactomannan gum. Tookey and Jones (1965. Economic Botany 19:165-174) surveyed 300 species in 139 genera in 31 plant families and concluded that: ". . . it is reasonable to expect that an annual legume will be found that can be developed into a domestic crop source of seed gum." The work resulted in U.S. Pat. No. 3,116,281 for the legume *Crotalaria intermedia*, but little else.

Buckeridge et al. (2000. op. cit.) also encouraged searching for a suitable legume, as well as using molecular techniques. The U.S. Patent Application 20040143871 by Dhugga (2004) describes an extensive molecular attempt to produce a variety of galactomannan gums in a variety of plants, with soybean and corn as the primary targets for a domestic source, although he does not name any specific target tissue.

Other than molecular work, no attempt has been made to produce gum in soybean, although Whistler and Saarnio (1957. J. Am. Chem. Soc. 79(22):6055-6057) suggested recovering a trivial yield of galactomannan from waste soybean hulls of unspecified cultivars available at the time, despite that they did not know the tissue containing the galactomannan, and were unaware of any genetic based variability in yield. A similar report by Aspinall and Whyte (1964. J. Chem. Soc. 232:5058-5063) also did not lead to gum production. None of these authors measured the endosperm. The reason for the lack of interest, is that soybean has been considered to have virtually no endosperm, and therefore virtually no galactomannan (Chalon. 1875. Societe Sci. Arts Lettres Hainaut. 10:3-66; Nadelmann (1890. op. cit.); Pammel 1899. Trans. Acad. Sci. St. Louis 9(6):91-273+xxxv ic; Kirkbride et al. 2003. Fruits and seeds of genera in the subfamily Faboideae (Fabaceae). USDA ARS Technical Bulletin 1890. v+1-1218; Buckeridge et al. (2000. op. cit.); Dhugga (2004. U.S. patent application 20040143871); Ma et al. 2004. Can. J. Bot. 82:654-662.). Even though hybridization of soybean with other species in the genus *Glycine* has been practiced for almost a hundred years (Hymowitz and Singh. 1987. 23-48 in Caldwell, B. E., ed. Soybeans: improvement, production, and uses. Second edition. ASA, CSSA, and SSSA, Madison, Wis.), there has been no attempt to create a cultivated soybean by transferring traits for enlarged endosperm from the wild relatives or landraces, because all prior research indicates such breeding attempts would not lead to larger endosperm. As an example of the indications in the prior research in which endosperm was misidentified as non-endosperm tissue, Yaklich et al. (1989. Crop. Sci. 1304-1309) surveyed the wild species and the cultivated soybean, and inferred in a table that the size of this tissue in wild species was smaller than in the cultivated soybean. Any reader, correctly identifying this tissue as endosperm, would thus conclude that any breeding attempts for endosperm involving wild relatives would likely result in a smaller endosperm in the cultivated plant.

This unfulfilled need for a large endosperm in soybean means that such transgenic methods as Dhugga (2004. U.S. patent application 20040143871) have several disadvantages: (a) transgenic methods add complexity; (b) a non-endosperm target tissue for expression must be chosen, and therefore a suitable and likely novel processing system must be developed and implemented for extraction; and (c) for culinary uses especially, many people are opposed to materials developed by transgenic means.

As shown in the above background section, there really is no prior art for the assessment, enlargement, or subsequent use of soybean endosperm, although there may be some aspects of knowledge and previous techniques that may be adaptable in pursuit of such a goal.

Accordingly, several objects and advantages of the invention are:

(a) to create an enlarged endosperm tissue in a cultivated soybean for the production of natural gums;

(b) to maintain an endosperm tissue of suitable size in a plant with other agronomically desirable traits;

(c) to create an enlarged endosperm tissue in a cultivated soybean which can be utilized for the production of modified gums and other materials;

(d) to create an enlarged endosperm tissue in a cultivated soybean from which materials can be extracted easily;

(e) to create an enlarged endosperm tissue in a cultivated soybean which can be used for chemical and physical manipulation for altered agronomic traits; and (f) to develop a system for galactomannan and other material production and extraction that gives good yield and minimally interferes with normal soybean processing.

Further objects and advantages will become apparent from a consideration of the ensuing description and drawings.

SUMMARY

It has been believed since almost the beginning of scientific study of legume endosperm (Schleiden and Vogel. 1839. Nova Acta Acad. Caesar. Leop.-Carol. 19(l):53-96+6 ic.) that mature dormant soybean seeds have virtually no endosperm (Nadelmann. 1890. Prings. Jarhb. Wissen. Bot.21:609-691+6 ic.; Pammel. 1899. Trans. Acad. Sci. St. Louis 9(6):91-273+ xxxv ic. Kopooshian and Isely. 1966. Iowa Acad. Sci. 73:59-67; Buckeridge et al. 2000. 283-316 in Gupta and Kuar, eds. Carbohydrate Reserves in Plants—Synthesis and Regulation. Elsevier.; Kirkbride et al. 2003. Fruits and seeds of genera in the subfamily Faboideae (Fabaceae). USDA ARS Technical Bulletin 1890. v+1-1218), with the understanding that all legumes possess endosperm to some degree (Lackey. 1981. Bot. Gaz. 142(1):160-164). It has also been believed that endosperm in other species of *Glycine*, which are the wild relatives of the soybean, is equally insignificant (Yaklich et al. 1989. Crop. Sci. 1304-1309; Kirkbride et al. 2003. op. cit.). My studies show that both of these beliefs are incorrect: cultivated soybean has a small, although apparently completely functional three-layer endosperm, and many wild relatives and landraces have endosperm that is much larger; often in absolute terms, and certainly in proportion to total seed size, than the cultivated plants.

This misunderstanding occurred for several reasons, among them: (a) many researchers performed wet dissections, which tend to degrade the galactomannan-containing endosperm tissue, thus obscuring its size and structure; (b) researchers have not correctly identified the endosperm tissue, and thus measured the wrong tissue or measured it incorrectly; (c) researchers identified the endosperm tissue, but incorrectly regarded it as having unknown function and features peculiar and unique to the genus *Glycine* and thus did not even consider it for commercial use; (d) the correlation between cotyledon areoles and endosperm was not recognized, and thus researchers heretofore could not use cotyledon areoles as a guide to finding galactomannan-containing endosperm: (e) researchers did not know the exact location to perform dissections to see endosperm, so they could not detect endosperm presence and size; and (f) the research was conducted virtually independently in three different disciplines, agronomy, botany, and biochemistry, with little communication among them.

With knowledge that galactomannan-containing endosperm of diverse size exists in soybean and wild relatives in the genus *Glycine*, and with techniques to determine the size of endosperm, one can combine these with use of well-established hybridization techniques to select suitable parents, make crosses, and select offspring with a desirable size of endosperm. Transgenic and other techniques may be substituted for hybridization to give equivalent results. Growing and harvesting of soybean seed is a highly developed and well-known technology. This can be further combined with technology for extraction of materials from legume endosperm because such technology is well developed for guar, locust, fenugreek, and other legumes.

SHORT DESCRIPTION OF THE DRAWINGS

DETAILED DESCRIPTION OF THE INVENTION

Figure 1:
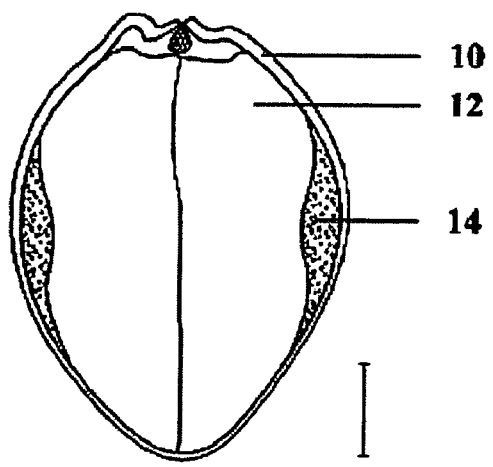
FIG. 1 is a camera lucida drawing of a dormant mature seed of *Glycine* gracilis PI 86046 in cross section made by dry dissection. Scale bar equals one millimeter.

I have discovered a way to enlarge endosperm tissue in cultivated soybean, *Glycine max*. I have also discovered that this large endosperm tissue can be used as a place from which naturally occurring, and introduced, gums and other materials can be easily extracted during processing. Because the production, processing, and technology of soybean is highly developed in the United States and other countries, the production of gum and other materials by my method is better than current production methods of similar gums and other materials from other legumes, which are not generally cultivated in the United States.

Legume seed gums are primarily found in, or at least most easily extracted from, the endosperm. These legume galactomannan endosperm gums; called endosperm gums, legume gums, galactomannan gums, galactomannans, or simply gum, among other terms; are part of a worldwide market of a wide range of hydrophilic natural and synthetic gums. These are highly desirable for thousands of food and industrial purposes. Current plant sources of legume seed gum, such as guar and locust bean, are generally cultivated outside the United States. The availability of these gums is often uncertain, and subject to unpredictable market and political factors. Development of a stable domestic source, such as from soybeans, would be desirable.

Unfortunately, mature soybean seeds have been reported to have no endosperm or virtually no endosperm, and thus have heretofore not been considered as a likely source of galactomannan gum. Detailed structure of these gums is known for only a few legumes (Buckeridge et al. 2000. 283-316 in Gupta and Kuar, eds. Carbohydrate Reserves in Plants—Synthesis and Regulation. Elsevier). They are presumed to consist of a mannose backbone with galactose side branches, in various combinations, even within a single seed. Variants may also include additional sugar forms and other materials and combinations. When the galactose side branches are few, the galactomannans are often referred to as mannans. In this application, the term galactomannan refers to all these forms and any other related forms.

I have discovered that the nature of endosperm in soybean has been subject to much misunderstanding by scientists, even in recent years. Because of this misunderstanding, there has been no method attempted to develop or increase soybean endosperm and employ it towards useful purposes. It has long been believed that endosperm tissue in soybean and relatives is scant or nonexistent. Some recent scientists, such as Thorne (1981. Plant Physiol. 67: 1016-1025.), even incorrectly believed that this scant tissue is not even endosperm, but rather maternal tissue, which has different genetic, developmental, and structural features, and thus would not likely be useful for gums. Other researchers, Ma et al. (2004. Can. J. Bot. 82: 654-662), Yaklich et al. (1989. Crop Sci. 29: 1304-1309, 1996. Seed Sci. Res. 6: 183-189.), believed that the soybean endosperm tissue structure is unique to soybean, or at least the genus *Glycine*, and has some unknown function. In particular, the table in Yaklich et al. (1989. op. cit.), which inferred that the size of the endosperm, although misidentified, of wild species of *Glycine* was smaller than the endosperm in the cultivated soybean, was misleading. I have discovered through my observations, and through a careful re-reading, that they were not measuring the size of the endosperm, but rather measuring another surface feature, and thus the conclusion that wild species have smaller endosperm than the cultivated soybean is incorrect.

Millers and other agricultural workers also have misunderstandings of endosperm. Millers have known of low levels of galactomannan content in the "hull." Millers use the term "hull" for the exterior of the soybean seed removed in processing. Although they are unaware of its nature, the "hull" is the seed coat 10, also known as testa, (FIG. 2), with adherent endosperm 14. Such low levels are not regarded as useful, however, but rather are regarded as non-nutritional or antinutritional components and are undesirable. Some galactomannans are also reported from the embryo cotyledons 12, often referred to as "endosperm" in milling. The embryo galactomannans are also regarded as undesirable soybean components in animal feed, because they are indigestible and cause other nutritional problems, and are difficult to remove from the embryo. Many efforts have taken place to degrade galactomannans in soybean-based animal feeds. Thus, although the presence of soybean galactomannans is known, they are not extractable or purifiable (in the embryo), or are not in sufficient and pure quantities (in the "hull") to be used for commercial purposes.

I developed several new tools and techniques to examine microscopically legume seeds related to soybeans. I developed cutting blocks and end cutters to make fast dissections and cross sections of dry seeds, as opposed to the wet dissections used by most researchers, which cause the endosperm to swell, and then the included material to dissolve, so the endosperm extent and nature cannot be observed accurately. Several hundred samples of seeds, many of which are not readily available even to the scientific community, were examined in detail.

My findings show that previous interpretations of endosperm are inaccurate. My observations of soybean and relatives show that cultivated soybeans have the same endosperm structure as relatives, but the development of endosperm is reduced to such a degree that it is microscopic. FIG. 1 shows in cross section a seed of Glycine gracilis, a semi-wild relative of soybean.

Figure 2:
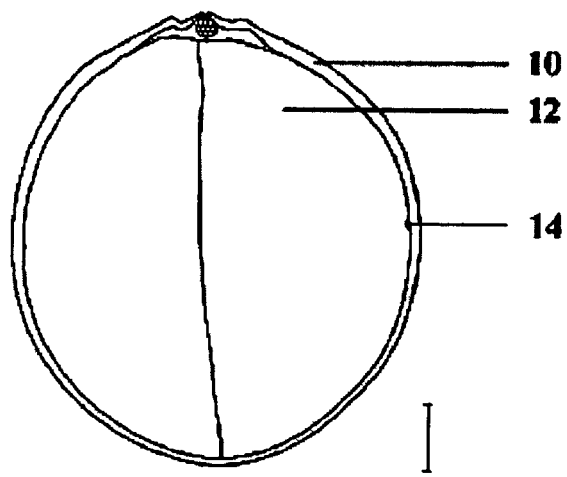
FIG. 2 is a camera lucida drawing of a dormant mature seed of *Glycine max* cultivar Williams in cross section made by dry dissection. Scale bar equals one millimeter.

Element 10 is the seed coat. A cotyledon 12, with its mirror image companion on the opposite side, are the major part of the embryo. The endosperm 14 appears outside of each cotyledon as a lateral packet of hard, glassy material, primarily of galactomannan gum in the cell walls. The endosperm remains adherent to the seed coat when the embryo is separated from the seed coat. FIG. 2 shows a Glycine max cultivar Williams, a modem North American soybean cultivar. The seed coat 10, although thinner, and the cotyledons 12, although thicker, are otherwise generally the same as in most wild relatives, but the expanded middle layer of the endosperm 14, in the genus Glycine referred to as an antipit by agricultural researchers, is only visible as a much reduced area. As with many legumes, soybean endosperm has three layers; an outer or aleurone layer, an inner layer of crushed cells, and a middle layer. It is the expansion of the middle layer in soybean that causes the appearance of the endosperm 14. Specifically, I discovered several new things:

1) The middle endosperm layer of almost all 22 genera of the tribe Glycininae, to which soybean (Glycine max of the genus Glycine) belongs, is highly developed (Table 1).

TABLE 1

Glycininae genera endosperm middle layer

| Genus | Middle layer | Species | Distribution |
|---|---|---|---|
| Neorautanenia | + | 1 | Africa |
| Eminia | + | 5 | Tropical Africa. |
| Pseudeminia | + | 4 | Tropical Africa. |
| Pseudovigna | + | 1 | Tropical Africa. |
| Sinodolichos | + | 2 | Asia |
| Pueraria | + | 20 | Asia. |
| Nogra | − | 3 | Asia. |
| Glycine | + | 19 | Asia and Australia. |
| Teramnus | + | 8 | Pantropical. |
| Teyleria | + | 1 | Asia. |
| Neonotonia | + | 1 | Africa to Asia. |
| Phylacium | + | 2 | Indochina, China and the Philippines to N. Queensland |
| Neocollettia | ? | 1 | Burma and Java |
| Herpyza | ? | 1 | Cuba |
| Cologania | + | 10 | Mexico, Central and South America |

TABLE 1-continued

Glycininae genera endosperm middle layer

| Genus | Middle layer | Species | Distribution |
|---|---|---|---|
| Amphicarpaea | −/+ | 3 | Asia, Africa, North America |
| Dumasia | + | 8 | Asia and Africa. |
| Calopogonium | + | 8 | Neotropics |
| Pachyrhizus | + | 6 | Neotropics |
| Diphyllarium | + | 1 | Indochina |
| Mastersia | + | 2 | Indo-Malaya |
| Shuteria | + | 5 | Indo-Malaya |

Middle layer:
+ = expanded,
− = not expanded,
? = unknown, specimens unobtainable;
species = number of species in genus;
distribution = natural distribution.

The few exceptions to a well developed middle endosperm layer all seem to have a logical explanation. The one species of Nogra examined is not a member of the Glycininae, but properly belongs to another sub-tribe, the Phaseolinae, characterized by lack of readily visible endosperm. The two species of Amphicarpaea that appear to lack a middle layer have highly specialized subterranean seeds and seed ecology that may have eliminated the need for endosperm gum storage. Within the genus Glycine, G. max superficially appears to be an anomaly that lacks endosperm; it is a cultivated species in which the expanded middle endosperm layer seems to have been reduced drastically over thousands of years of cultivation and selection. Virtually all of the information in Table 1 is new to science.

2) The three layers of soybean endosperm in the expanded middle layer area appear to be the same as found generally in many, if not most, legumes.

3) In modem cultivars of soybean the degree of development of the middle layer is highly reduced, often to a few dozen cells.

4) The middle endosperm layer of wild, semi-wild, and some old cultivars of Glycine species is often highly developed into hundreds, if not thousands, of cells, and is spread over a larger area than in other cultivated soybeans.

5) The middle endosperm layer of cultivated soybeans and relatives is strongly water absorbing, as I observe under the microscope, and as I would expect from similar galactomannan containing endosperm in many legumes. My observations differ from those of previous workers, who use the standard wet method for dissections, which distorts or destroys the endosperm layer by the time observations are made. Ma et al. (2004. op. cit.) also observed the destruction of cell impression patterns on the inner endosperm layer upon addition of water, but did not relate this to galactomannan.

Figure 3:
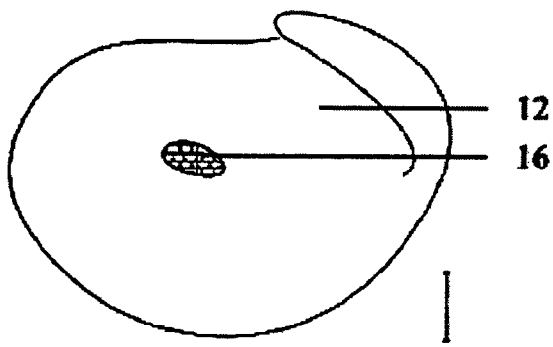
FIG. 3 is a camera lucida drawing of a dormant mature seed embryo of *Glycine* gracilis PI 135590 lateral view made by dry dissection. Scale bar equals one millimeter.

6) Opposite the middle endosperm layer of cultivated soybean is a layer of enlarged cells on the outer cotyledon 12 surface called a pit or cotyledon areole 16 (FIG. 3). A virtually identical cotyledon areole is present in other members of the Glycininae that have a well-developed middle endosperm layer. Those few species, previously mentioned, that lack a middle endosperm layer lack the cotyledon areole. Because soybean has a cotyledon areole, this is convincing evidence that the tissue opposite the pit in cultivated soybean is a reduced middle endosperm layer. And this cotyledon areole can be used as a guide to locate an expanded middle endosperm layer, which, because it is usually clear and colorless, may be difficult to see against the testa inner surface.

With my above described discoveries, I have been able to find members of the genus *Glycine* with large endosperm tissue, and have developed a method of increasing the size of cultivated soybean endosperm tissue by using relatives of soybean with abundant endosperm. I have also developed new uses of the tissue as a place of expression for naturally occurring and introduced materials in high yield.

The method to increase the amount of the middle endosperm layer in cultivated soybeans is by standard cross pollination technique with wild species with which soybean can be crossed. The techniques of making such appropriate crosses of the cultivated soybean with its wild relatives is well known to those with ordinary skill in plant breeding, once one knows which wild plants should be crossed with the cultivated soybean and to what purpose. The easiest method of selecting wild relatives with abundant middle endosperm layers is by cracking dry seeds in half through the hilum with a razor blade and a specially made guide block, electronics end cutter, or similar tool, and observing under a dissecting microscope to see the view shown in FIG. 1 or FIG. 2. Abundant endosperm 14, of FIG. 1, is detectable by the glassy appearance of such tissue on each side of the cotyledons. Crossing with soybean, which shows scant endosperm 14 of FIG. 2, produces more abundant endosperm in the offspring similar to those in FIG. 1, element The following examples are meant to be descriptive and by no means limiting of the various embodiments and aspects of the present invention.

EXAMPLE 1

Measuring Methods

Assessment of endosperm size and relative size is most readily accomplished by dry dissection of mature seed. Wet methods, as employed by Kirkbride et al. (2003. op. cit.) and many others, cause loss in galactomannan mass and structure, especially the cotyledon areole impression on the endosperm.

A dissecting microscope with a measuring graticule and the usual instruments of the art are needed. In addition, to crack or cut the seeds, a user needs a modified electronics end cutter and a custom cutting block to be used with a single-edge razor blade. The miniature electronics end cutter should have an oblique end 50 to 70 degrees, and must be resharpened to be flush on the back side, with no micro bevel, and with less than a 30 degree bevel on the other. The cutting block is made of fine-grain wood or other suitable material about 25 mm×25 mm×15 mm. Two or three grooves or channels of various widths and depths, suitable to fit seeds, are formed in parallel across the flat upper surface. Perpendicular to these grooves or channels is made one saw cut, starting in the middle and to a depth about half the thickness of the block, with a kerf just large enough to allow a single-edge razor blade to slide. To crack a seed, the electronics end cutter holds the seed in a suitable position, while the user observes under a microscope, and with modeling clay packed to prevent seed loss, the user squeezes the handles and hears an audible pop when the seed cracks. Using a similar technique under the microscope, the cutting block kerf is used as a guide for the single-edge razor blade and the grooves are used as a positioner for the seed while the cut is made. Clay is also used for packing, and an audible pop is similarly heard when the seed cracks.

Measurement of overall seed size and weight can be made by usual methods known to those skilled in the art. Measurement of endosperm can generally be made readily from the seeds cut in cross section through the middle of the hilum, or slightly (0-20% of hilum length) towards the posterior (lens) end (all seed orientation terms are per Sterling (1954. Bull. Torrey Bot. Club 81(4):271-287)). In *Glycine* seeds the greatest expansion of endosperm, occurs in this medial position opposite the mid-vein of each cotyledon. In many cultivated soybeans, the small size of the expanded endosperm requires an additional step, because a cross section cut is unlikely to cut through the most enlarged part of the endosperm. In these instances, the seed is cut in longitudinal section. The testa is pried from the embryo half, starting at the hilum, the strongest part of the testa. The testa is observed on the inner surface. Any endosperm will adhere to the inside of the testa. An impression of the cells of the cotyledon areole will be found in a medial position as shown by photographs in Ma et al. (2004. op. cit.). At the point of the cotyledon areole impression will be the thickest development of endosperm. A cut through the testa at this point will allow measurement of the expanded middle layer in cross section.

Because seeds vary greatly in size, several methods exist for comparing relative sizes of endosperm. Kopooshian (1963. Seed character relationships in the Leguminosae. Ph.D. dissertation. Iowa State University) dissected embryos and endosperm, weighed both, and compared the two. He abandoned this as tedious, and not much more accurate than simple comparison under the microscope, and the use of descriptive terms of thickness. Nadelmann (1890. op. cit.) compared the thickness of endosperm to testa thickness. Although this is quick, it has the disadvantage of emphasizing testa thickness, which does not necessarily correlate with overall seed size. Kirkbride et al. (2003. op. cit.) used descriptive terms, which are subject to subjectivity. The method used here uses a ratio, called here a ML/W, compares the thickness of the endosperm, at this position usually consisting primarily of the expanded middle layer and minute amounts of aleurone layer and inner layer, on both sides of the embryo to the overall thickness, or width, of the seed. To place this into context, a theoretical seed that consisted of two expanded endosperm layers each half the thickness of the seed, and thus the entire seed consisting only of endosperm, would have a ML/W (middle layer to seed width) ratio of 1.00. Another example is a random sample of guar, which has copious endosperm and yields about 40% galactomannan by weight commercially, and has a ML/W ratio of 0.44. *Glycine max*, *G. soja*, and *G. gracilis* seeds measured so far have ML/W from 0.01 to 0.21. In *Glycine* seeds, the middle layer in this technique is measured along with the inner endosperm layer and aleurone layer, with which it is indistinguishable by the methods used here. Using compound microscopy or other techniques, the combined aleurone layer and inner layer are known to be about 0.03 mm thick, so even with no expansion of the middle layer, there will be a ML/W of 0.005 to 0.01 in these seeds. Thus, on the lowest range of endosperm development in *Glycine*, at ML/W =0.01, there is virtually no expansion of middle endosperm layer.

EXAMPLE 2

Available Endosperm Sources

Modem scientifically bred cultivars have very little endosperm as has been repeatedly noted. For instance, cultivar Williams (Specimen Beltsville 2002 at BARC, cf. Holmgren et al. 1990. Index herbariorum. x+693 pp. New York Botanical Garden. Bronx, New York, for location abbreviations. All USDA Plant Introduction, PI numbers, cited here are available from the USDA National Soybean Research Center, Urbana, Illinois. All modern cultivars are commonly available from commercial or public sources.) with a seed width of 6.8 mm and a middle layer endosperm thickness at each side of about 0.06 mm gives a middle layer to width ratio (ML/W) of 0.02, about half of which is accounted for by the aleurone and inner endosperm layers. Measurements for cultivars Clark and Harovinton in micrographs of Ma et al. (2004. op. cit.) are comparable with cultivar Williams.

Baker and Minor (1987. Crop. Sci. 27:1301-1303) misidentified endosperm tissue. They measured what they referred to as "endothelium" thickness, which in my studies is identified as endosperm thickness, in 127 out of 378 randomly chosen accessions of USDA-ARS soybean accessions. In the remaining 251 accessions they could find no expanded endosperm. Thickness in the 127 samples ranged from 0.08 to 0.22 mm. One may suggest that endosperm in the 251 accessions were smaller, and thus below the level of detection using their methods.

My review of all 92 samples chosen by Chen and Nelson (2004. Crop Sci. 44(1): 316-325)) showed the availability of nontrivial amounts of endosperm in wild relatives of soybean. They chose samples of 31 Plant Introductions (PI numbers) of *Glycine soja*, the wild form of the soybean; 30 samples of *Glycine gracilis*, a semi-wild form intermediate between the wild form and the cultivated soybean; and 31 samples of land races of *Glycine max*, the cultivated soybean. The samples chosen by Chen and Nelson were all wild collected or represent cultivated plants prior to scientific breeding. Because the wild, semi-wild, and cultivated plants, freely interbreed it is sometimes difficult to place a specific sample into one of the three categories, and to some extent the categories and assignments should be regarded as artificial (Lackey (1981) 301-327 in Polhill and Raven, eds. Advances in legume systematics. part 1. xvi+425+xxi. Royal Botanic Gardens. Kew). In the current application, the term cultivated soybean means G. max, the common soybean of commerce and agriculture: the scientific names G. soja and G. gracilis refer to the wild and semiwild forms. A summary of endosperm size found is given in Table 2.

TABLE 2

Endosperm size in *Glycine soja*, *G. gracilis*, and *G. max* (old cultivars).

| Species | Function | Seed mg | ML mm | ML/W |
|---|---|---|---|---|
| G. soja | Avg | 17 | 0.15 | 0.13 |
|  | Min | 8 | 0.10 | 0.08 |
|  | Max | 28 | 0.22 | 0.18 |
| G. gracilis | Avg | 53 | 0.21 | 0.14 |
|  | Min | 22 | 0.10 | 0.04 |
|  | Max | 102 | 0.35 | 0.21 |
| G. max | Avg | 136 | 0.16 | 0.07 |
|  | Min | 89 | 0.02 | 0.01 |
|  | Max | 268 | 0.37 | 0.18 |

All data from 92 samples chosen by Chen and Nelson (2004).
Function:
Avg = average,
Min = minimum,
Max = maximum;
Seed mg = seed weight in milligrams;
ML mm = middle endosperm layer thickness in millimeters (includes aleurone and inner endosperm layers);
ML/W = middle endosperm layer to seed width ratio.

In general, the wild and semi-wild soybeans have the largest endosperm thickness relative to seed width and largest in absolute terms, although several potential sources exist within old cultivar specimens assigned to *Glycine max*, and these several potential sources distort averages. Eight specimens with the largest endosperm are given in Table 3.

TABLE 3

Large endosperm specimens in Chen and Nelson (2004).

| Species | Seed mg | ML mm | ML/W | Source |
|---|---|---|---|---|
| Glycine max | 129 | 0.37 | 0.15 | M86 *G. max* PI 68728 Northeast China |
| Glycine soja | 20 | 0.22 | 0.18 | S64 *G. soja* PI 522182B Heilongjiang China |
| Glycine max | 95 | 0.34 | 0.18 | M74 *G. max* PI 437119 Primorye Russia |
| Glycine gracilis | 24 | 0.21 | 0.18 | G46 Semi-wild PI 291275 Heilongjiang China |
| Glycine gracilis | 30 | 0.24 | 0.19 | G39 Semi-wild PI 291309C Heilongjiang China |
| Glycine gracilis | 43 | 0.29 | 0.19 | G01 Semi-wild PI 417139 Tohoku Japan |
| Glycine gracilis | 46 | 0.32 | 0.19 | G25 Semi-wild PI 417138 Tohoku Japan |
| Glycine gracilis | 65 | 0.35 | 0.21 | G34 Semi-wild PI 86046 Hokkaido Japan |

Specimens with endosperm ML/W ratios > 0.17 or ML mm > 0.32.
Seed mg = seed weight in milligrams;
ML mm = middle endosperm layer thickness in millimeters (includes aleurone and inner endosperm layers);
ML/W = middle endosperm layer to seed width ratio;
Source = Chen and Nelson designation, PI number, and place of collection.

Although survey of the 92 samples gives an idea of the range of potential gene donors for enlarged endosperm, it only represents a tiny portion of the thousands of pre-scientific breeding samples available under Plant Introduction numbers and from other sources.

EXAMPLE 3

Endosperm Size is Heritable

A cross of a modern soybean cultivar with a wild soybean shows that endosperm size is heritable and can result in a cultivated soybean with enlarged endosperm, if one can appropriately alter the genetics of the plant and measure the endosperm of the resultant seed. The results (F2 generation) of a cross between soybean cultivar Dwight x *Glycine soja* PI 518282 is shown in table 4.

TABLE 4

Heritability *Glycine max* cultivar Dwight x *Glycine soja* PI 518282.

| Plant | Seed mg | ML mm | ML/W |
|---|---|---|---|
| Glycine soja PI 518282 | 18 | 0.18 | 0.14 |
| F2 | 77 | 0.19 | 0.09 |
| Glycine max cv Dwight | 129 | 0.09 | 0.04 |

All numbers as averages of 6 seeds each, on all thickened endosperm middle layers.
Seed mg = seed weight in milligrams;
ML mm = middle endosperm layer thickness in millimeters (includes aleurone and inner endosperm layers);
ML/W = middle endosperm layer to seed width ratio.

The F2 seeds from the cross are intermediate in size, shape, color, and other characters from the parents. They are also intermediate, or even larger, in endosperm size, both in absolute terms (from 0.09 mm in the cultivated soybean and 0.18 mm in PI 518282 to 0.19 mm in the F2) and relative size (from 0.04 in the cultivated soybean and 0.14 in PI 518282 to 0.09 in the F2). Several points are notable about this cross. This cross was designed for purposes other than showing heritability of endosperm size, and other parents would likely have shown an even more pronounced inheritance in terms of size of endosperm. Many wild plants have larger endosperm than PI 518282, and most modem soybean cultivars have smaller endosperm than cultivar Dwight. Nonetheless, the cross clearly shows heritability and production of a cultivated or semi-cultivated soybean with expanded endosperm, containing the same glassy, water soluble gum as found in the parents and many other legumes.

EXAMPLE 4

Use of Middle Endosperm Layer

I have also discovered a new use of the expanded middle endosperm layer in soybean as a tissue for the easy expression and extraction of high yields of natural galactomannan gum and other materials, if one selects or creates those plants having large capacity endosperm and removes material from the endosperm.

For example, a random single seed sample of the plant PI 68728 assigned to *Glycine max*, was selected. This PI 68728 was selected to be likely to be high yielding by the method given under the heading "Measuring methods." The random sample was weighed at various stages of dissection. The whole seed weighed 131.4 milligrams. Upon dissection, the embryo weighed 116.8 milligrams; the testa and adherent endosperm 13.5 milligrams; the remaining 1.1 milligrams was dissection loss. Dissection removal of the expanded middle layer of endosperm, apparently almost pure galactomannan, with small amounts of other materials, resulted in a weight of 1.4 milligrams. This gives a yield of endosperm material of over 1% of the whole seed weight, which would be higher if the minor additional amounts of inner endosperm material lining the inner testa were added to the yield. The yield given here is much higher than the about 0.14% yield experienced by Whistler and Saarnio (1957. J. Am. Chem. Soc. 79(22):6055-6057) on soybean hulls of common commercial varieties, assuming a hull weight of common commercial varieties of about 7% of seed weight (Wolf et al. 2002. Cereal Chem. 79(3):439-444). Whistler and Saarnio were unaware of the tissue source of the gum, or any method of increasing the tissue. Although the given example with PI 68728 was accomplished with dissection, to those of skill in milling, there are a variety of mechanical and chemical production methods of removing material from soybean hulls and determining yield.

This gum appears to have similar properties to guar gum and locust bean gum. Because the endosperm and the associated galactomannans remains adherent to the seed coat in all my observations, and because the embryo has no physical tissue connection with the endosperm or seed coat, it can be removed easily from both, as is experienced by millers with the commercial soybean. The embryo can enter commercial processing flow as is currently practiced for current modem cultivars. The seed coats and the adherent endosperm, however can enter a processing stream for gum extraction, or for extraction of any other material produced in the endosperm. Because galactomannan natural development is relatively specific to the endosperm, identification of the tissue specific promoter or promoters for its production allows for production of a variety of materials in the endosperm tissue when the promoter or promoters are associated with genetic sequences of interest, and thus my method is not limited to galactomannan extraction, but can be used to yield high amounts of many materials.

Accordingly the reader will see that the development of an enlarged endosperm in a cultivated soybean and the use of high yielding soybean endosperm has several advantages for commercial production of galactomannan gum and other materials. My way is superior to current sources of galactomannan gums for the following reasons:

1) Soybean cultivation and processing is highly developed, familiar, and productive in the United States and other countries. Addition of a soybean gum component or other endosperm-bearing components to the cultivation and processing stream can be handled with minimum disruption. Other sources, such as guar and locust bean, are mostly grown outside the United States, less productive, and will cause more difficulties than with soybean, because their technologies are not as well known.

2) Soybeans are well-known to the American, Asian, and other consumers, and are regarded as a healthy and safe foodstuff. A product that is derived from soybeans, such as a natural soybean gum will be favorably received, particularly for foodstuffs. Other legume sources of gum are not as familiar and are not so favorably received.

3) The enlarged soybean endosperm tissue is a better place than other tissues of soybean or other crop plants for the expression of a variety of materials, such as industrial gums, whether natural, or introduced by conventional breeding or genetic engineering. Plant breeding, genetics, and the technology of soybeans is better developed than with any other legume, and thus can be more readily adapted to these uses.

4) Extraction of materials from soybean endosperm, which is removed with the seed coat in milling, leaves the embryo intact for other purposes. Thus the addition of an endosperm product, whether for food or industrial purposes, is likely to have minimal impact on the usual processing of embryos for oil, feed, etc.

While the above description contains many specificities, these should not be construed as limitations on the scope of the invention, but as exemplifications of the presently preferred embodiments thereof. Many other ramifications and variations are possible within the teachings of the invention. For example:

1) One could enlarge the endosperm tissue by methods other than conventional breeding. For instance, one could alter the genetics of soybean directly to increase the growth or size of the endosperm tissue. One could also transfer genes, in their natural or altered form, from a non-soybean plant to the cultivated soybean, which would increase the endosperm tissue. Such transgenic breeding programs are now routine components of modern soybean technology.

2) Instead of enlarging the middle endosperm layer, one could increase the amount of the outer, aleurone layer, or the inner layer, or any other component or combination of components of the endosperm.

3) One could use the natural galactomannan gum from soybean, or could alter the genetics of soybean directly, or introduce foreign genes, which would cause the expression of a variety of galactomannans or other materials in the endosperm, which would be especially useful for industrial purposes.

4) Instead of enlarging the endosperm of soybean, the method can be easily adapted to maintaining or reducing the size of the endosperm to a desirable size commensurate with other desirable traits.

5) Those skilled in the art will be able to develop readily many alternate simple or complex methods of destructive and non-destructive measurement of endosperm tissue, including extraction of galactomannan gum or other materials and measurement of yield, assessment of a variety of physical and chemical properties of endosperm or its contents, assessment of mass density of the seeds, and observation of a wide variety of other seed attributes that may be confirmed to correlate in some way with endosperm extent.

6) Those skilled in the art will be able to develop readily many means of milling soybean seed and seed parts for optimal removal of materials from endosperm. These would include the usual cracking, screening, blowing, pin milling, etc.

Thus the scope of the invention should be determined by the appended claims and their legal equivalents, and not by the examples given.

That which is claimed:

1. A method to get an enlarged endosperm in seeds in a *Glycine max* plant, said method comprising the steps of:
   (a) altering genome of said plant;
   (b) determining size of said endosperm in seeds of said plant; and
   (c) selecting seeds with an enlarged endosperm.

2. The method of claim 1, wherein said method further comprises removing of said endosperm from seed of said plant.

3. The method of claim 1, wherein said method further comprises extracting material or materials from said endosperm.

4. The method of claim 1, wherein said altering genome of said plant is accomplished by sexual reproduction.

5. The method of claim 4, wherein sexual reproduction is accomplished by crossing cultivated soybean, *Glycine max*, with wild plants of the genus *Glycine*.

6. The method of claim 1, wherein said determining size of said endosperm includes determining size of the endosperm from dry seed dissections.

7. The method of claim 1, wherein said determining size of said endosperm includes locating a cotyledon areole.

8. A method for obtaining a desirable yield of material or materials from endosperm in seeds of a *Glycine max* plant, said method comprising the steps of:
   (a) comparing the size of endosperm in seeds between said plant and a second genetically distinct *Glycine max* plant;
   (b) selecting plant with an enlarged endosperm; and
   (c) removing said material or materials from seeds of selected plant.

9. The method of claim 8, wherein said desirable yield is greater than one percent of weight of said seeds.

10. The method of claim 8, wherein said material or materials are galactomannan.

11. A method of obtaining material or materials from endosperm in seeds from a *Glycine max* plant, said method comprising the steps of:
    (a) identifying plants with an enlarged endosperm;
    (b) growing selected plants under conditions for production of said material or materials;
    (c) harvesting said endosperm; and
    (d) extracting said material or materials from said endosperm.

12. The method of claim 11, wherein said material or materials are galactomannan.

13. The method of claim 11, wherein said material or materials are polysaccharide.

14. A method to get an enlarged endosperm in seeds in a *Glycine max* plant, said method comprising the steps of:
    (a) altering the genome of said plant;
    (b) locating the endosperm by using cotyledon areoles as guidance and determining size of said endosperm in seeds of said plant; and
    (c) selecting plants with an enlarged endosperm.

15. A method to get an enlarged endosperm in seeds in a *Glycine max* plant, said method comprising the steps of:
    (a) altering the genome of said plant;
    (b) locating the endosperm of the seed and determining the size of the endosperm;
    (c) selecting plants with an enlarged endosperm and cross breeding the selected plants; and
    (d) locating the endosperm of seeds of resulting crosses and selecting seeds with enlarged endosperm.

16. A method to enlarge endosperm size in seeds in a *Glycine max* plant, said method comprising the steps of:
    (a) locating the endosperm by using cotyledon areoles as guidance and determining the size of the endosperm from dry dissections of seeds of *Glycine max* plants;
    (b) selecting plants with an enlarged endosperm and cross breeding the selected plants; and
    (c) locating the endosperm of seeds of resulting crosses by using cotyledon areoles as guidance and selecting seeds with enlarged endosperm.

* * * * *